United States Patent [19]
Schroeder et al.

[11] Patent Number: 5,410,060
[45] Date of Patent: Apr. 25, 1995

[54] PROCESS FOR PREPARATION OF ARENEBISPHOSPHINE OXIDES

[75] Inventors: Jochen Schroeder, Limburgerhof; Wolfgang Siegel, Mannheim; Matthias Lokai, Enkenbach-Alsenborn, all of Germany

[73] Assignee: BASF Aktiengesellschaft, Ludwigshafen, Germany

[21] Appl. No.: 160,153

[22] Filed: Dec. 2, 1993

[30] Foreign Application Priority Data

Dec. 5, 1992 [DE] Germany ............ 42 40 964.0

[51] Int. Cl.⁶ .............. C07F 9/30; C07F 9/53; C07F 9/40
[52] U.S. Cl. ...................... 546/21; 548/111; 548/412; 549/5; 549/6; 568/14; 568/15; 522/64
[58] Field of Search ............ 568/15, 14; 522/64; 546/21; 548/111, 412; 549/5, 6

[56] References Cited

U.S. PATENT DOCUMENTS

| | | | |
|---|---|---|---|
| 2,900,408 | 8/1959 | Blaser et al. | 260/161 |
| 4,298,738 | 11/1981 | Lechtken et al. | 546/22 |
| 4,324,744 | 4/1982 | Lechtken et al. | 260/932 |
| 4,447,520 | 4/1984 | Henne et al. | 430/281 |
| 4,737,593 | 4/1988 | Ellrich et al. | 568/15 |
| 4,792,632 | 12/1988 | Ellrich et al. | 568/15 |
| 5,296,636 | 3/1994 | Siegel et al. | 568/323 |

FOREIGN PATENT DOCUMENTS

| | | |
|---|---|---|
| 0007508 | 2/1980 | European Pat. Off. |
| 0057474 | 6/1982 | European Pat. Off. |
| 0073413 | 3/1983 | European Pat. Off. |
| 0184095 | 6/1986 | European Pat. Off. |
| 1010965 | 6/1957 | Germany. |

OTHER PUBLICATIONS

Morrison & Boyd, *Organic Chemistry*, p. 445, Allyn & Bacon, 1959.

Primary Examiner—Susan W. Berman
Attorney, Agent, or Firm—Oblon, Spivak, McClelland, Maier & Neustadt

[57] ABSTRACT

Arenebisphosphine oxides of the general formula

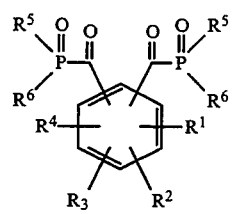

where $R^1$ to $R^4$ independently of one another are each hydrogen, $C_1$–$C_6$-alkyl, $C_1$–$C_6$-alkoxy, $C_5$–$C_{10}$-aryl, $C_5$–$C_{12}$-aryloxy or $C_7$–$C_{14}$-arylalkoxy, $R^5$ and $R^6$ independently of one another may each be $C_1$–$C_6$-alkyl, $C_5$–$C_{10}$-cycloalkyl or $C_5$–$C_{12}$-aryl, each of which may furthermore contain one or two nitrogen or sulfur atoms in the ring system or carry one or two halogen atoms or $C_1$–$C_6$-alkyl or $C_1$–$C_6$-alkoxy groups as substituent on the ring system, or $C_1$–$C_6$-alkoxy, $C_3$–$C_8$-alkoxyalkoxy, $C_5$–$C_{12}$-aryloxy or $C_7$–$C_{14}$-arylalkoxy, or $R^5$ and $R^6$ together form a bridge of 2 to 10 carbon atoms, in which some of the carbon atoms may furthermore be part of an aromatic ring.

7 Claims, No Drawings

PROCESS FOR PREPARATION OF ARENEBISPHOSPHINE OXIDES

The present invention relates to arenebisphosphine oxides of the general formula

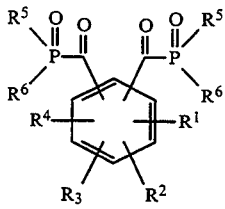

where $R^1$ to $R^4$ independently of one another are each hydrogen, $C_1$–$C_6$-alkyl, $C_1$–$C_6$-alkoxy, $C_5$–$C_{12}$-aryl, $C_5$–$C_{12}$-aryloxy or $C_7$–$C_{14}$-arylalkoxy, $R^5$ and $R^6$ independently of one another may each be $C_1$–$C_6$-alkyl, $C_5$–$C_{10}$-cycloalkyl or $C_5$–$C_{12}$-aryl, each of which may furthermore contain one or two nitrogen or sulfur atoms in the ring system or carry one or two halogen atoms or $C_1$–$C_6$-alkyl or $C_1$–$C_6$-alkoxy groups as substituent on the ring system, or are each $C_1$–$C_6$-alkoxy, $C_3$–$C_8$-alkoxyalkoxy, $C_5$–$C_{12}$-aryloxy or $C_7$–$C_{14}$-arylalkoxy, or $R^5$ and $R^6$ together form a bridge of 2 to 10 carbon atoms, in which some of the carbon atoms may furthermore be part of an aromatic ring.

The present invention furthermore relates to photopolymerizable materials which contain the arenebisphosphine oxides and the use of these materials as coating materials, for example as a surface coating or printing ink, as filling compound, as a dental material, as an adhesive or for the production of moldings, for example printing plates or relief plates.

Conventional photoinitiators for the polymerization of ethylenically unsaturated compounds are, for example, aromatic ketones, such as acetophenone and benzophenone derivatives, thioxanthones, benzoin ethers and benzil ketals. However, materials cured with such initiators exhibit undesirable yellowing which does not permit their use with the addition of white pigments. A further disadvantage is the small thickness of the cured layer.

It was possible to achieve an improvement with acylphosphine oxides, as described in, for example, EP-B-57 474 or EP-A-73 413.

The bisacylphosphine oxides disclosed in EP-A-184 095 are insufficiently soluble in photopolymerizable materials and are therefore difficult to process.

In general, there is a need for very reactive photoinitiators.

More highly reactive photoinitiators make it possible to reduce the amount sufficient for curing which is added to photopolymerizable materials. In particular, the curing rate also increases with increasing reactivity. This advantage is of particular importance in the production procedure conventionally used today, in which the photopolymerizable materials are placed on a conveyor belt and conveyed under a radiation source. With shorter curing times, the speed of the conveyor belt can be raised and the throughput thus increased.

It is an object of the present invention to provide photoinitiators which have very high reactivity and do not lead to yellowing of the cured materials.

We have found that this object is achieved by the arenebisphosphine oxides defined above and their use as photoinitiators in photopolymerizable materials.

In the arenebisphosphine oxides of the general formula I, $R^1$ to $R^4$ independently of one another are each preferably hydrogen, $C_1$–$C_6$-alkyl or $C_1$–$C_6$-alkoxy. $R^1$ to $R^4$ are each particularly preferably hydrogen or $C_1$–$C_4$-alkyl. In particular, the arenebisphosphine oxides are derived from mesitylene, so that one of the radicals $R^1$ to $R^4$ is hydrogen and the remaining radicals are each $C_1$–$C_4$-alkyl, preferably methyl, the $C_1$–$C_4$-alkyl being in the meta position relative to one another on the aromatic ring.

Examples of $R^1$ to $R^4$ are hydrogen as well as methyl, ethyl, isopropyl, n-propyl, n-butyl, amyl, n-hexyl, cyclopentyl, cyclohexyl, methoxy, ethoxy, propoxy, isopropoxy, butoxy, ethoxyethoxy or aryloxy, such as phenoxy, methylphenoxy or benzyloxy.

$R^5$ and $R^6$ independently of one another are each preferably $C_1$–$C_6$-alkyl, $C_1$–$C_6$-alkoxy or $C_5$–$C_{12}$-aryl. $R^5$ and $R^6$ are particularly preferably $C_1$–$C_4$-alkoxy or a phenyl ring.

Examples of possible radicals $R^5$ or $R^6$ are ethyl, isopropyl, n-propyl, n-butyl, amyl, n-hexyl, cyclopentyl, cyclohexyl, aryl, such as phenyl, naphthyl, halogen-substituted aryl, such as mono- or dichlorophenyl, alkyl-substituted phenyl, such as methylphenyl, ethylphenyl, isopropylphenyl, tert-butylphenyl or dimethylphenyl, alkoxy-substituted aryl, such as methoxyphenyl, ethoxyphenyl or dimethoxyphenyl, S- or N-containing five- or six-membered rings, such as thiophenyl or pyridyl, alkoxy, such as methoxy, ethoxy, isopropoxy, butoxy or ethoxyethoxy, or aryloxy, such as phenoxy, methylphenoxy or benzyloxy.

Examples of arenebisphosphine oxides are
1,3-bis(diphenylphosphonocarbonyl)benzene,
1,3-bis(diethoxyphosphonocarbonyl)benzene,
1,3-bis(ethoxyphenylphosphonocarbonyl)benzene,
or the corresponding 1,2- or 1,4-substituted derivatives,
1,3-bis(diphenylphosphonocarbonyl)-2,4,6-trimethoxybenzene,
1,3-bis(diethoxyphosphonocarbonyl)-2,4,6-trimethoxybenzene,
1,3-bis(ethoxyphenylphosphonocarbonyl)-2,4,6-trimethoxybenzene,
1,3-bis(diphenylphosphonocarbonyl)-2,4,6-trichlorobenzene,
1,3-bis(diethoxyphosphonocarbonyl)-2,4,6-trichlorobenzene,
1,3-bis(ethoxyphenylphosphonocarbonyl)-2,4,6-trichlorobenzene,
or compounds having the structures

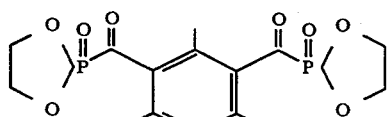

or

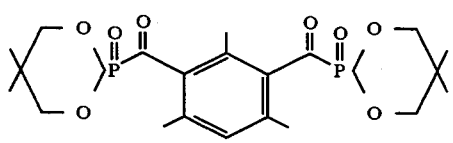

In the preparation of the arenebisphosphine oxides, it is possible to start from compounds of the formula

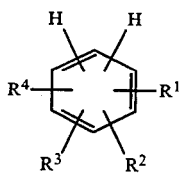   II $R^1$ to $R^4$ have the abovementioned meanings. The compound II is very particularly preferably mesitylene (1,3,5-trimethylbenzene).

The compound of the formula II can be converted into the bishaloacetophenone of the formula

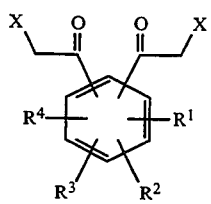   III by reaction with an α-haloacetyl halide, in particular an α-haloacetyl chloride, eg. chloroacetyl chloride or bromoacetyl chloride, in the presence of iron(III) oxide as catalyst and at from 0° to 150° C., preferably from 50° to 100° C., and from 0.01 to 50, preferably from 0.5 to 5, bar. The reaction can be carried out in the presence or absence of a solvent. Examples of suitable solvents are aromatic compounds, such as nitrobenzene or chlorobenzene, halogenated alkanes, such as dichloroethane or dichloromethane, or alkanes, such as hexane or heptane.

For the introduction of two haloacetyl groups, at least 2 mol of α-haloacetyl halide are used per mol of compound II.

The starting components are preferably used in a molar ratio of from 2:1 to 20:1 (α-haloacetyl halide: compound II), particularly preferably in stoichiometric ratios.

The compound III obtained can be converted into the dicarboxylic acid of the formula

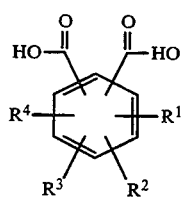   IV by haloform cleavage.

The haloform cleavage of the compound III is preferably carried out in an alkali metal hypohalite solution in the presence of a phase transfer catalyst at from 0° to 150° C., preferably from 30° to 80° C., particularly preferably from 40° to 70° C., and from 0.01 to 50, preferably from 0.1 to 5, bar, particularly preferably at atmospheric pressure. The alkali metal hypohalite solution can be used as such but may also be produced in situ during the reaction from an alkali metal hydroxide solution and a halogen, such as chlorine or bromine, preferably chlorine.

Suitable alkali metal hydroxides are lithium hydroxide, sodium hydroxide, potassium hydroxide, rubidium hydroxide and cesium hydroxide, particularly preferably sodium hydroxide and potassium hydroxide. The molar ratio of alkali metal hypohalite to compound III can be varied within wide limits and is as a rule from 0.8:1 to 50:1, preferably from 1:1 to 20:1, particularly preferably from 1:1 to 5:1.

Advantageous phase transfer catalysts are quaternary salts, in particular catalysts of the formula

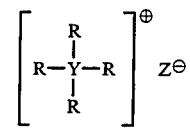

where the individual radicals R may be identical or different and, independently of one another, are each an aliphatic, cycloaliphatic, aromatic or araliphatic radical, Y is nitrogen, phosphorus or arsenic and Z is an anion. In preferred catalysts, R is alkyl or alkoxy, each of 1 to 18, in particular 1 to 7, carbon atoms, cycloalkyl of 5 to 8 carbon atoms, aralkyl, alkylaryl of 7 to 12 carbon atoms or phenyl.

The anion $Z^\ominus$ can be derived, for example, from mineral acids, such as hydrochloric acid, sulfuric acid, phosphoric acid, sulfonic acids, such as benzene- and p-toluenesulfonic acid, or from carboxylic acids, in particular mono-, di- or trichloroacetic acid.

The dicarboxylic acid is then converted into the bisacyl chloride of the formula

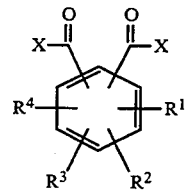   V which can be effected by a conventional reaction with thionyl chloride.

Finally, the arenebisphosphine oxides are obtained by reaction with a phosphine of the general formula

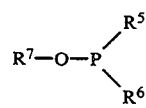   VI where $R^5$ and $R^6$ have the abovementioned meanings and $R^7$ is $C_1$-$C_6$-alkyl, $C_5$-$C_{10}$-cycloalkyl or $C_1$-$C_6$-alkoxy.

Examples of suitable phosphines are methyldimethoxyphosphine, butyldimethoxyphosphine, phenyldimethoxyphosphine, tolyldimethoxyphosphine, phenyldiethoxyphosphine, tolyldiethoxyphosphine, phenyldibutoxyphosphine, tolyldibutoxyphosphine or dimethylmethoxyphosphine, dibutylmethoxyphosphine, dimethylbutoxyphosphine, diphenylmethoxyphosphine, diphenylethoxyphosphine, diphenylpropoxyphosphine, diphenylisopropoxyphosphine, diphenylbutoxyphosphine or trimethyl phosphite, triethyl phosphite, tripropyl phosphite, triisopropyl phosphite and tributyl phosphite.

The reaction between the bisacyl chloride and the phosphine can be carried out in a solvent, for example a hydrocarbon or hydrocarbon mixture, such as petroleum ether, toluene or cyclohexane, an ether or another conventional inert organic solvent or in the absence of a solvent, at from −30° to 150° C., preferably from 10° to 100° C. The product can be crystallized directly from the solvent or remains behind after the evaporation.

In the reaction, the starting materials can be used in stoichiometric ratios since an excess of one of the starting components is generally unnecessary owing to the good conversion.

The arenebisphosphine oxides can be used as photoinitiators in photopolymerizable materials.

Such photopolymerizable or radiation-curable materials contain photopolymerizable ethylenically unsaturated compounds.

Suitable photopolymerizable monomers are compounds having polymerizable C—C double bonds which are activated, for example, by aryl, carbonyl, amino, amido, ester, carboxyl or cyano groups, halogen atoms or further C—C double or C—C triple bonds. Examples are vinyl ethers and vinyl esters, styrene, vinyltoluene, acrylic acid and methacrylic acid and esters thereof with monohydric and polyhydric alcohols, their nitriles or amides, maleates and fumarates and N-vinylpyrrolidone, N-vinyl-caprolactam, N-vinylcarbazole and allyl esters, such as diallyl phthalate.

Examples of photopolymerizable relatively high molecular weight compounds are unsaturated polyesters based on $\alpha,\beta$-unsaturated dicarboxylic acids, such as maleic acid, fumaric acid or itaconic acid, if required as a mixture with saturated or aromatic dicarboxylic acids, such as adipic acid, phthalic acid, tetrahydrophthalic acid or terephthalic acid, and alkanediols, such as ethylene glycol, propylene glycol, butanediol, neopentylglycol or oxyalkylated bisphenol A.

(Poly)epoxide (meth)acrylates, as are obtainable by reacting acrylic acid or methacrylic acid with diglycidyl ethers, or polyester (meth)acrylates or urethane (meth)acrylates are also important.

The photopolymerizable materials contain the novel compounds in general in a concentration of 0.001 to 20%, preferably 0.1 to 5%, by weight, based on the polymerizable material.

The arenebisphosphinoxides can be combined with accelerators which counteract any inhibitory effect of the atmospheric oxygen on the photopolymerization.

Such accelerators or synergistic agents are, for example, secondary and/or tertiary amines, such as methyldiethanolamine, dimethylethanolamine, triethylamine, triethanolamine, ethyl p-dimethylaminobenzoate, benzyldimethylamine, dimethylaminoethyl acrylate, N-phenylglycine, N-methylglycine and similar compounds known to the skilled worker. Aliphatic and aromatic halides, such as 2-chloromethylnaphthalene or 1-chloro-2-chloromethylnaphthalene or free radical formers, such as peroxides and azo compounds, may also be used for accelerating the curing.

Mixtures of the arenebisphosphine oxides with known photoinitiators may also be used. When such mixtures are used, synergistic effects are observed in some cases.

Particularly effective synergistic mixtures are obtained on combination with known photoinitiators based on aromatic ketones, in particular benzil dimethyl ketal, hydroxyisobutyrophenone, diethoxyacetophenone, benzophenone, 2-methylthioxanthone, 2-isopropylthioxanthone and 2-chlorothioxanthone.

The novel photopolymerizable materials which contain the arenebisphosphine oxides have a very good shelf life.

The photopolymerizable materials can be used as coating materials, for example as a surface coating or printing ink, or for the production of moldings, for example printing plates, photoresists or relief plates.

Furthermore, the photopolymerizable materials can be used as fillers. The abovementioned materials based on unsaturated polyesters or (poly)epoxide (meth)acrylates are also suitable for this application.

A further possible use is as dental compositions, for example as dental filling materials or dentures.

The photopolymerizable materials may also be solutions or dispersions, in particular aqueous dispersions, which contain photopolymerizable compounds. The photopolymerizable materials may contain additives customary for the intended use, for example dyes or pigments when used as a surface coating.

Examples of further additives are thermal polymerization inhibitors, leveling agents, fillers and dulling agents, as well as stabilizers against thermal or photochemical decomposition.

The radiation sources used for the light which initiates the polymerization of such mixtures are those which emit light preferably in the absorption range of the novel compounds, ie. in particular between 230 and 450 nm. Low pressure, medium pressure and high pressure mercury lamps and fluorescent tubes or pulsed lamps are particularly suitable.

The novel photoinitiators can be used to cure photopolymerizable materials, in particular white-pigmented surface coatings, without giving rise to yellowing. Furthermore, the novel photoinitiators possess high reactivity. The curing times of the photopolymerizable materials are considerably reduced as a result of the high reactivity of the arenebisphosphine oxides.

EXAMPLES

I. Preparation of the arenebisphosphine oxides

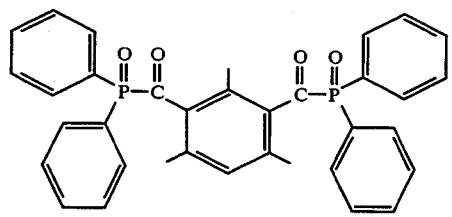

A)

1,3-Bis(diphenylphosphonocarbonyl)-2,4,6-trimethylbenzene

In the first stage, 240 g of 1,3,5-trimethylbenzene and 160 mg of $Fe_2O_3$ were initially taken and heated to 80° C. A total of 503 g of chloroacetyl chloride were added in the course of one hour. Shortly after the beginning of the addition, the catalyst $Fe_2O_3$ dissolved completely with the production of a red color, and evolution of HCl began simultaneously. After 50% of the theoretical amount of HCl had been liberated, the passing of nitrogen through the reaction mixture was begun.

After the end of gas evolution, 5 g of water were added to the reaction mixture and distillation was carried out under reduced pressure. The product 1,3-bis(chloroacetyl)-2,4,6-trimethylbenzene had a boiling point of 140° C. at 0.3 mbar and a melting point of 129°–131° C. The yield was 376 g.

In the second stage, 500 g of sodium hypochlorite solution (13% by weight of active chlorine), 720 g of 25% strength sodium hydroxide solution and 4 g of dimethyldibenzylammonium chloride as a 50% strength aqueous solution were initially taken and heated to 50° C. Thereafter, 85 g of 1,3-bis(chloroacetyl)-2,4,6-trimethylbenzene were added. A further 66 g of chlorine gas were passed in for one hour, after which stirring was carried out for 5 hours at the reflux temperature (about 105°–108° C.).

After cooling to room temperature, the reaction solution was discharged and was brought to pH 2 with about 200 ml of concentrated hydrochloric acid. The white suspension was filtered and the precipitate was washed with twice 250 ml of water and dried at 80° C. under reduced pressure.

61.5 g of 2,4,6-trimethylbenzene-1,3-dicarboxylic acid were obtained.

In the third stage, 85 g of thionyl chloride were initially taken and heated to 40° C. 57.3 g of 2,4,6-trimethylbenzene-1,3-dicarboxylic acid were added to this in the course of 45 minutes. Stirring was carried out at 40°–50° C. until the end of the evolution of gas.

The residue was distilled under reduced pressure, and 38 g of 2,4,6-trimethylbenzene-1,3-dicarbonyl dichloride having a boiling point of 113° C. at 1.4 mbar were obtained.

In the fourth stage, 34.3 g of 2,4,6-trimethylbenzene-1,3-dicarbonyl dichloride were initially taken at 80° C. 64.4 g of ethoxydiphenylphosphine were added in the course of one hour and stirring was carried out for a further hour at this temperature. 50 ml of xylene and 50 ml of mineral spirit were then added in succession. The product crystallized on slow cooling and was filtered off under suction and dried under reduced pressure.

The yield was 75 g of 1,3-bis(diphenylphosphonocarbonyl)-2,4,6-trimethylbenzene (melting point 164°–165° C.).

B)

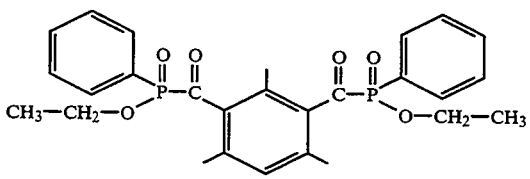

1,3-Bis(ethoxyphenylphosphonocarbonyl)-2,4,6-trimethylbenzene

The preparation in the first three stages was carried out as for A). In the fourth stage, 53 g of 2,4,6-trimethylbenzene-1,3-dicarbonyl dichloride and 74 g of diethoxyphenylphosphine were reacted similarly to stage 4 under A at 80° C. 107 g of liquid end product were obtained.

II. Testing of performance characteristics

Determination of the reactivity 4 g of the photoinitiator shown below were dissolved in 96 g of an oligoether acrylate based on a reaction product of alkoxylated trimethylolpropane with acrylic acid (Laromer ® LR 8812 from BASF). The photopolymerizable material was applied in a layer thickness of 50 g/m² to art paper and was transported on a conveyor belt under a high pressure mercury lamp (120 W/cm) at a distance of 30 cm.

The maximum possible speed of the conveyor belt at which curing still occurs is a measure of the reactivity of the photoinitiator.

| Photoinitiator | Maximum possible speed of the conveyor belt [m/min] |
| --- | --- |
| from Example I A | 20 |
| from Example I B | 20 |
| for comparison 2,4,6-Trimethylbenzoyl-diphenylphosphine oxide (Lucirin ® TPO from BASF) | 16 |

We claim:

1. A process for the preparation of an arenebisphosphine oxide of the formula I,

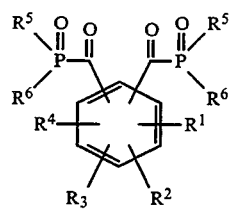

which comprises the following process steps:

a) introduction of two haloacetyl groups into a compound of the formula

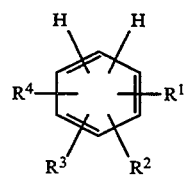

by means of an α-haloacetyl halide in the presence of iron (III) oxide, b) conversion of the bishaloacetophenone obtained in a) of the formula

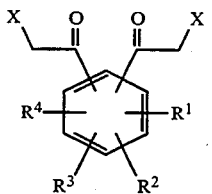

into the dicarboxylic acid of the formula

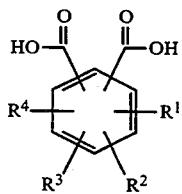

by reaction with an alkali metal hypohalite solution in the presence of a phase transfer catalyst, c) conversion of the dicarboxylic acid into the corresponding bisacyl chloride of the formula

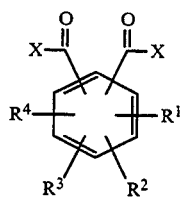

and d) reaction of the bisacyl chloride with a phosphine of the formula

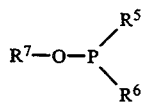

to give the arenebisphosphine oxide in which $R^1$ and $R^4$ independently of one another are each hydrogen, $C_1$–$C_6$-alkyl, $C_1$–$C_6$-alkoxy, $C_5$–$C_{12}$-aryl, $C_5$–$C_{12}$-aryloxy or $C_7$–$C_{14}$-arylalkoxy, $R^5$ and $R^6$ independently of one another are each $C_1$–$C_6$ alkyl, $C_5$–$C_{10}$-cycloalkyl or $C_5$–$C_{12}$-aryl, each of which may furthermore contain one or two nitrogen or sulfur atoms in the ring system or carry one or two halogen atoms or $C_1$–$C_6$-alkyl or $C_1$–$C_6$-alkoxy groups as substituent on the ring system, or are each $C_1$–$C_6$-alkoxy, $C_3$–$C_8$-alkoxyalkoxy, $C_5$–$C_{12}$-aryloxy or $C_7$–$C_{14}$-arylalkoxy, or $R^5$ and $R^6$ together form a bridge of 2 to 10 carbon atoms, in which some of the carbon atoms may furthermore be part of an aromatic ring and $R^7$ is a $C_1$–$C_6$-alkyl, $C_1$–$C_6$-cycloalkyl or $C_1$–$C_6$-alkoxy group.

2. A process as claimed in claim 1, wherein the compound of the formula II is mesitylene.

3. A process as claimed in claim 1, wherein said α-haloacetyl halide is an α-haloacetyl chloride.

4. A process as claimed in claim 1 wherein said α-haloacetyl halide is selected from the group consisting of chloroacetyl chloride and bromoacetyl chloride.

5. A process as claimed in claim 1 wherein process steps a) and b) are carried out at 0° to 150° C. and 0.01 to 50 bar.

6. A process as claimed in claim 1, wherein process step a) is carried out at 50° to 100° C. and 0.5 to 5 bar, and process step b) is carried out at 30° to 80° C., and 0.1 to 5 bar.

7. A process as claimed in claim 6, wherein process step b) is carried out at 40° to 70° C. and at atmospheric pressure.

* * * * *